(12) United States Patent
Sano et al.

(10) Patent No.: US 7,091,726 B2
(45) Date of Patent: Aug. 15, 2006

(54) ELECTROSTATIC CAPACITANCE SENSING DEVICE AND METHOD OF DRIVING THE SAME

(75) Inventors: Junichi Sano, Nagano (JP); Mitsutoshi Miyasaka, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 10/932,037

(22) Filed: Sep. 2, 2004

(65) Prior Publication Data

US 2005/0088185 A1  Apr. 28, 2005

(30) Foreign Application Priority Data

| Sep. 5, 2003 | (JP) | ............................. 2003-313930 |
| Sep. 5, 2003 | (JP) | ............................. 2003-313931 |
| Sep. 5, 2003 | (JP) | ............................. 2003-313932 |
| Sep. 5, 2003 | (JP) | ............................. 2003-313933 |
| Jun. 2, 2004 | (JP) | ............................. 2004-164499 |

(51) Int. Cl.
*G01R 27/26* (2006.01)

(52) U.S. Cl. ...................................... 324/661; 324/662

(58) Field of Classification Search ................ 324/661, 324/662; 382/124
See application file for complete search history.

(56) References Cited

U.S. PATENT DOCUMENTS

| 6,483,931 | B1 * | 11/2002 | Kalnitsky et al. ............ 382/124 |
| 6,512,381 | B1 * | 1/2003 | Kramer ....................... 324/658 |
| 6,731,120 | B1 * | 5/2004 | Tartagni ....................... 324/662 |
| 2004/0239342 | A1 * | 12/2004 | Yoshida et al. ............. 324/663 |
| 2005/0078856 | A1 * | 4/2005 | Miyasaka et al. ........... 382/124 |

FOREIGN PATENT DOCUMENTS

| JP | A 11-118415 | 4/1999 |
| JP | A 11-312811 | 11/1999 |
| JP | A 2000-346608 | 12/2000 |
| JP | A 2001-56204 | 2/2001 |
| JP | A 2001-133213 | 5/2001 |
| JP | A 2003-254706 | 9/2003 |
| JP | A 2004-89675 | 3/2004 |
| JP | A 2004-102511 | 4/2004 |

OTHER PUBLICATIONS

"Low Temperature Poly-Si TFTs on Plastic Substrate Using Surface Free Technology by Laser Ablation/Annealing (SUFTLA)", Utsunomiya et al., SID 00 Digest, Seiko Epson Cororation, Suwa, Japan, 2000.

* cited by examiner

*Primary Examiner*—Walter Benson
(74) *Attorney, Agent, or Firm*—Oliff & Berridge, PLC (57) ABSTRACT

An electrostatic capacitance sensing device of exemplary embodiments of the present invention include M number of row lines, N number of column lines that are arranged in a matrix of M rows and N columns, N number of path gates for output signal, and electrostatic capacitance sensing elements provided at the intersections between the row and column lines. The electrostatic capacitance sensing element includes a signal sensing element, a signal amplifying element, a column selection element, and a row selection element. The signal sensing element includes a capacitance sensing electrode and a capacitance sensing dielectric film. The path gate for output signal, the signal amplifying element, the column selection element, and the row selection element are made up of thin-film semiconductor devices.

16 Claims, 8 Drawing Sheets

ELECTROSTATIC CAPACITANCE SENSING DEVICE AND METHOD OF DRIVING THE SAME

BACKGROUND OF THE INVENTION

1. Field of Invention

The present invention relates to an electrostatic capacitance sensing device that reads the surface contours of a fingerprint or other target object having extremely small ridges and valleys, by sensing electrostatic capacitance, which changes according to the distance from the surface of the target object.

2. Description of Related Art

Figure 1:
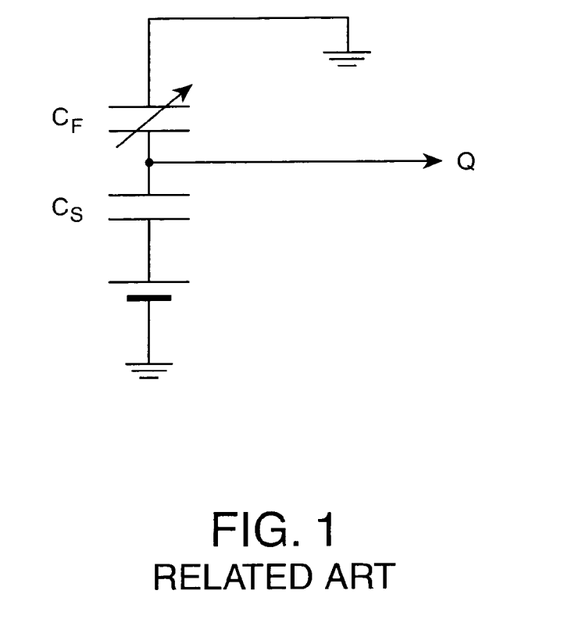
FIG. 1 is a schematic that shows an electrostatic capacitance sensing device applying related art operational principle.

Japanese Unexamined Patent Publications No. 11-118415, No. 2000-346608, No. 2001-56204, No. 2001-133213 disclose that related art electrostatic capacitance sensing devices, that are used in fingerprint sensors and so forth, a sensor electrode and a dielectric deposited on the sensor electrode, can be formed on a single-crystal silicon wafer. The principle of operation of a related art electrostatic capacitance sensing device is shown in FIG. 1. One of a pair of electrodes in a capacitor is a sensor electrode, and the other is grounded to a human. Furthermore, a dielectric is formed on the uppermost surface of the electrostatic capacitance sensing device. The capacitance $C_F$ of this capacitor changes according to the ridges and valleys in a fingerprint contacting the surface of the dielectric. Meanwhile, the semiconductor substrate is equipped with a capacitor that forms electrostatic capacitance $C_s$. These two capacitors are coupled in series, and a predetermined voltage is applied. The application of a voltage causes a charge Q corresponding to the ridges and valleys in a fingerprint to be formed between the two capacitors. This charge is sensed using ordinary semiconductor technology and the surface contours of the target object are read.

SUMMARY OF THE INVENTION

However, the related art electrostatic capacitance sensing devices are formed on a single-crystal silicon wafer. Hence, they are fragile and subject to breaking when too much finger pressure is applied if they are used as a fingerprint sensor.

In addition, fingerprint sensors, because of the application, need to be approximately 20 mm×20 mm in size. The majority of the area of the electrostatic capacitance sensing device is occupied by the sensor electrode. The sensor electrode is, of course, formed on a single-crystal silicon wafer, yet the majority of the single-crystal silicon wafer (under the sensor electrode), the creation of which requires enormous energy and labor, serves as nothing more than a supporting member. In other words, the related art electrostatic capacitance sensing devices are not only expensive, they create huge waste and expense. Moreover, in a related art electrostatic capacitance sensing device, the sensing sensitivity is poor since an extremely small charge Q needs to be read. Since the charge Q is determined according to the capacitance of a dielectric, if the thickness of a dielectric, which also functions as a protective film of the device, is increased, the charge Q becomes further smaller. In other words, if the sensing sensitivity is enhanced in a related art electrostatic capacitance sensing device, a protective film (dielectric) becomes thin such that the endurance of the device deteriorates.

Moreover, it has been strongly suggested that personal identification functions ought to be provided on cards such as credit cards and bank cards to increase card security. However, related art electrostatic capacitance sensing devices that are made on a single-crystal silicon wafer lack flexibility and, therefore, cannot be formed on a plastic substrate.

Accordingly, exemplary embodiments of the present invention provide a superior electrostatic capacitance sensing device that operates stably, can reduce the expenditure of unnecessary energy and labor during manufacture, and can be made on a substrate other than a single-crystal silicon wafer, and a method of driving the same.

In addition, exemplary embodiments of the present invention are also designed to provide an excellent electrostatic capacitance sensing device that has high sensing sensitivity even if a protective film is thickened so as to enhance or improve the endurance of the device.

Exemplary embodiments of the present invention include an electrostatic capacitance sensing device reading the surface contours of a target object by sensing electrostatic capacitance, which changes according to the distance from the target object. The electrostatic capacitance sensing element includes M number of row lines (the row line of the i-th row is represented as $RL_i$ where i is an integral number from 1 to M), and N number of column lines (the column line of the j-th column is represented as $CL_j$ where j is an integral number from 1 to N) that are arranged in a matrix of M rows and N columns. The sensing device also comprises x number of power-supply lines (the power-supply line of the i-th row is represented as $PL_i$ where i is a given integral number), y number of output lines (the output line of the j-th column is represented as $OL_j$ where j is a given integral number), and electrostatic capacitance sensing elements (the electrostatic capacitance sensing element located at the i-th row and the j-th column is represented as $ECSE_{ij}$) provided at the intersection between each row line ($RL_i$) and each column line ($CL_j$). The electrostatic capacitance sensing element ($ECSE_{ij}$) includes a signal sensing element ($SSE_{ij}$), a signal amplifying element ($SAE_{ij}$), a row selection element ($RSE_{ij}$), and a column selection element ($CSE_{ij}$). The signal sensing element ($SSE_{ij}$) includes a capacitance sensing electrode and a capacitance sensing dielectric film. The signal amplifying element is an MIS type thin-film semiconductor device to amplify signal ($MIS\text{-}SA_{ij}$) that includes a gate electrode, a gate insulation film, and a semiconductor film. The row selection element is an MIS type thin-film semiconductor device for row selection ($MIS\text{-}RS_{ij}$) that includes a gate electrode, a gate insulation film, and a semiconductor film. The column selection element is an MIS type thin-film semiconductor device to select column ($MIS\text{-}CS_{ij}$) that includes a gate electrode, a gate insulation film, and a semiconductor film.

In addition, in the sensing device, the MIS type thin-film semiconductor device to amplify signal ($MIS\text{-}SA_{ij}$), the MIS type thin-film semiconductor device for row selection ($MIS\text{-}RS_{ij}$), and the MIS type thin-film semiconductor device to select column ($MIS\text{-}CS_{ij}$) are preferably coupled to each other in series. Moreover, the gate electrode of the MIS type thin-film semiconductor device to amplify signal ($MIS\text{-}SA_{ij}$) is preferably coupled to the capacitance sensing electrode. The gate electrode of the MIS type thin-film semiconductor device for row selection ($MIS\text{-}RS_{ij}$) is preferably coupled to the row line ($RL_i$). The gate electrode of the MIS type thin-film semiconductor device to select column ($MIS\text{-}CL_{ij}$) is preferably coupled to the column line ($CL_j$). In addition, the number of power-supply lines, x, preferably satisfies $M/2 \leq y \leq M$. The number of output lines, y, preferably satisfies $N/2 \leq y \leq N$. Furthermore, in the sensing device, a row selection signal is supplied to the row line (RL$_i$) so as to select certain one row from M number of rows, and a column selection signal is supplied to the column line (CL$_j$) so as to select certain one column from N number of columns. Then, power is supplied to the electrostatic capacitance sensing element (ECSE$_{ij}$) so as to extract an output from the output line. Thereby, the surface contours of a target object is obtained from each of electrostatic capacitance sensing elements arranged in a matrix of M rows and N columns.

According to exemplary embodiments of the present invention, in addition to the above configuration, N number of pathgates for output signal (the pathgate for output signal of the j-th column is represented as PG-OL$_j$ where j is an integral number from 1 to N) are further provided. The pathgate for output signal (PG-OL$_j$) is an MIS type thin-film semiconductor device for output signal pathgate (MIS-PG$_j$) that includes a gate electrode, a gate insulation film, and a semiconductor film. In addition, the row line (RL$_i$) may have the combination of a function to select the MIS type thin-film semiconductor device for row selection (MIS-RS$_{ij}$) and a function of a power-supply line for supplying power to an electrostatic capacitance sensing element.

According to exemplary embodiments of the present invention, thin-film semiconductor devices can constitute an electrostatic capacitance sensing element with high sensitivity. In related art electrostatic capacitance sensing devices, the size thereof is at most approximately several millimeters by several millimeters on a plastic substrate due to using a single-crystal silicon wafer. Exemplary embodiments of the present invention, however, can provide an electrostatic capacitance sensing device having an area some 100 times larger than the related art devices, on a plastic substrate, and moreover, is capable of extremely high-accuracy sensing of ridge and valley information in a target object. As a result, exemplary embodiments of the present invention can be used, for example, to markedly enhance or improve the security level of a smart card. Furthermore, in a related art electrostatic capacitance sensing device formed on a single-crystal silicon wafer, only an extremely small portion of the device area actually uses the single-crystal silicon semiconductor so that a tremendous amount of energy and labor are uselessly wasted. In contrast, exemplary embodiments of the present invention eliminate this extravagant waste so as to contribute to conservation of the global environment.

DETAILED DESCRIPTION OF PREFERRED EMBODIMENTS

In exemplary embodiments of the present invention, MIS type thin-film semiconductor devices include metal-insulator-semiconductor films consitutute an electrostatic capacitance sensing device that reads the surface contours of a target object by sensing electrostatic capacitance, which changes according to the distance from a target object. Thin-film semiconductor devices are inexpensively fabricated as large sized semiconductor integrated circuits due to being formed on inexpensive glass substrates, and for example, used as liquid crystal display devices. Therefore, fabricating an electrostatic capacitance sensing device applied to a fingerprint sensor and so forth with thin-film semiconductor devices obviates the need to use an expensive substrate such as a single-crystal silicon wafer, whose production consumes tremendous energy. Instead, the device can be fabricated inexpensively on glass without wasting precious global resources. In addition, a semiconductor integrated circuit made up of thin-film semiconductor devices can be fabricated on a plastic substrate by applying the transfer technology referred to as SUFTLA as disclosed in related art document Japanese Unexamined Patent Publication No. 11-312811 and by S. Utsunomiya et. al in Society for Information Display, p. 916 (2000).

Under current thin-film semiconductor device technology, it is impossible to use thin-film semiconductor devices to produce an electrostatic capacitance sensing device shown in FIG. 1 that operates on related art principles. The charge Q that is induced between two capacitors coupled in series is extremely small. The charge Q can be read if single-crystal silicon LSI technology, which enables high-sensitivity sensing, is used. However, the charge Q cannot be accurately read with thin-film semiconductor devices. The reasons are, inferiority of the transistor characteristics in a thin-film semiconductor to that of single-crystal silicon LSI technology, and a large degree of deviation in characteristics among thin-film semiconductor devices.

In order to overcome the above issue, an electrostatic capacitance sensing device of exemplary embodiments of the present invention includes M number of row lines (the row line of the i-th row is represented as RL$_i$ where i is an integral number from 1 to M), and N number of column lines (the column line of the j-th column is represented as CL$_j$ where j is an integral number from 1 to N) that are arranged in a matrix of M rows and N columns. The sensing device also includes electrostatic capacitance sensing elements (the electrostatic capacitance sensing element located at the i-th row and the j-th column is represented as ECSE$_{ij}$) provided at the intersection between each row line (RL$_i$) and each column line ($CL_j$). The electrostatic capacitance sensing element ($ECSE_{ij}$) comprises a signal sensing element ($SSE_{ij}$), a signal amplifying element ($SAE_{ij}$), a row selection element ($RSE_{ij}$), and a column selection element ($CSE_{ij}$). The signal sensing element includes a capacitance sensing electrode and a capacitance sensing dielectric film. The voltage V is produced in the capacitance sensing electrode in response to electrostatic capacitance to be measured. In exemplary embodiments of the present invention, this voltage V is amplified by the signal amplifying element formed within each electrostatic capacitance sensing element and is converted to current. Specifically, the signal amplifying element is made up of an MIS type thin-film semiconductor device to amplify signal (MIS-$SA_{ij}$), including a gate electrode, a gate insulation film, and a semiconductor film. The gate electrode of the MIS type thin-film semiconductor device to amplify signal (MIS-$SA_{ij}$) is coupled to the capacitance sensing electrode.

Figure 2:
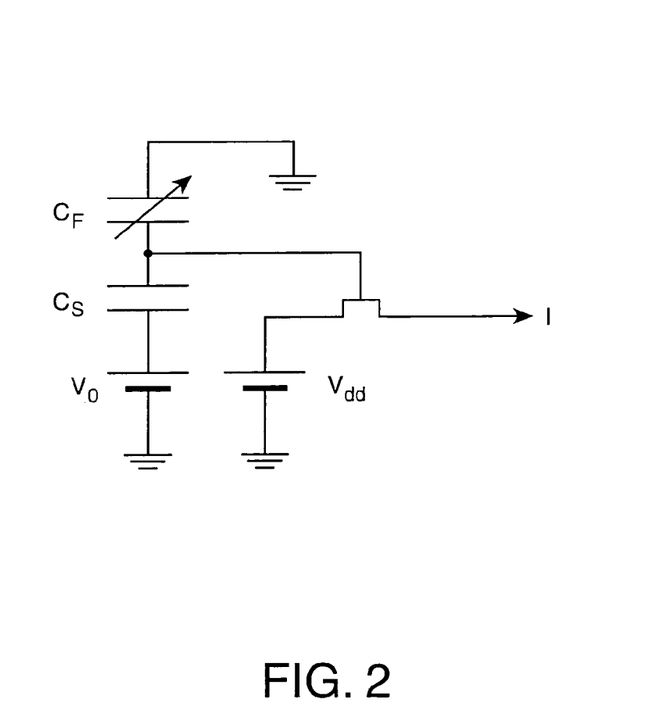
FIG. 2 is a schematic that shows an electrostatic capacitance sensing device applying the operational principle of exemplary embodiments of the present invention.

The operating principle of exemplary embodiments of the present invention is shown in FIG. 2. When a given voltage $V_o$ is applied between a capacitor having electrostatic capacitance $C_S$ and a capacitor having electrostatic capacitance $C_F$ that changes according to the surface contours of a target object, the voltage $V_o$ is divided according to the capacitance. The voltage V generated in this manner is utilized as the gate potential of the MIS type thin-film semiconductor device to amplify signal (MIS-$SA_{ij}$). If a given voltage is applied to the drain region of the thin-film semiconductor device in this state, the current I that flows between the source and the drain of the thin-film semiconductor device in proportion to the induced voltage V is markedly amplified. The charge Q itself that has been induced in the capacitance sensing electrode does not flow elsewhere but is retained. Hence, the measurement of the current I is also facilitated by raising drain voltage or by extending the length of measuring time and so forth. Consequently, the surface contours of a target object can be measured with sufficient accuracy even if a thin-film semiconductor device is used.

In exemplary embodiments of the present invention, the MIS type thin-film semiconductor device to amplify signal (MIS-$SA_{ij}$) is used as a signal amplifying element as described above. In this case, the MIS type thin-film semiconductor device to amplify signal (MIS-$SA_{ij}$) itself can also serve as a capacitor having electrostatic capacitance $C_S$. In other words, the transistor capacitance $C_T$ of the MIS type thin-film semiconductor device to amplify signal (MIS-$SA_{ij}$) serves as a new electrostatic capacitance in place of the electrostatic capacitance $C_S$. Such a design enables a capacitor having electrostatic capacitance $C_S$ to be eliminated from the electrostatic capacitance sensing element. Not only does this simplify the configuration, it also makes the fabrication process easier. In addition, consolidating the two power supplies depicted in FIG. 2 into a common power supply $V_{dd}$ is an effective way of eliminating superfluous wires within an electrostatic capacitance sensing device.

Figure 3:
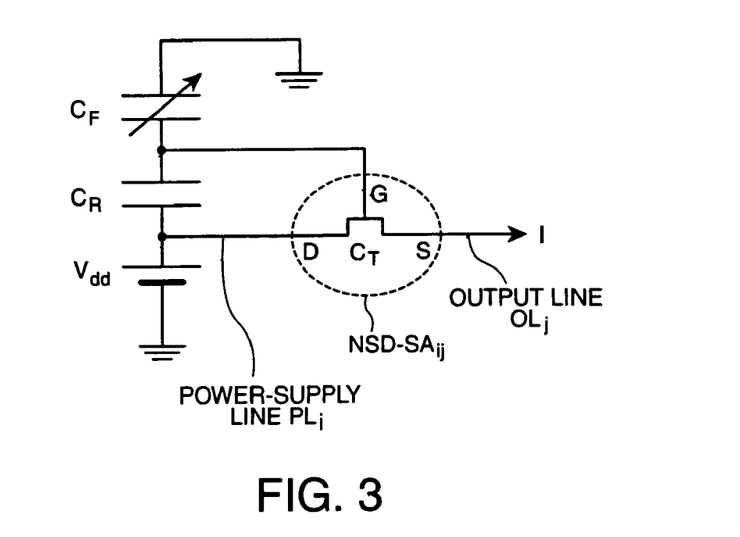
FIG. 3 is a schematic that shows an equivalent circuit diagram obtained when a common power supply is used for the electrostatic capacitance sensing device shown in FIG. 2.

The equivalent circuit diagram with respect to the principle of operation in this condition is shown in FIG. 3. A capacitor having electrostatic capacitance $C_F$, which changes according to the surface contours of the target object, and a capacitor (MIS type thin-film semiconductor device to amplify signal itself) having the transistor capacitance $C_T$ are coupled in series. Strictly speaking, the transistor capacitance $C_T$ is electrostatic capacitance that is formed between the drain electrode and gate electrode of the MIS type thin-film semiconductor device to amplify signal (MIS-$SA_{ij}$). To realize the configuration of FIG. 3 most easily, it is sufficient to couple the source region of the MIS type thin-film semiconductor device to amplify signal (MIS-$SA_{ij}$) to an output line ($OL_j$) and to couple the drain region of the MIS type thin-film semiconductor device to amplify signal (MIS-$SA_{ij}$) to a power-supply line ($PL_i$), whereupon a voltage $V_{dd}$ is applied to the power-supply line ($PL_i$), and a current I that changes according to the surface contours of the target object is extracted from the output line ($OL_j$). (In exemplary embodiments of the present invention, one of source and drain electrodes is referred to as a source and the other thereof is referred to as a drain for convenience. Accordingly, a source and a drain in exemplary embodiments of the present invention can be interchanged with each other always.) However, such a simple element configuration involves a problem that it takes a long time to output a signal, and information interferes with each other between electrostatic capacitance sensing elements. Thus, in exemplary embodiments of the present invention, an electrostatic capacitance sensing element includes an MIS type thin-film semiconductor device for row selection (MIS-$RS_{ij}$) as a row selection element ($RSE_{ij}$), and an MIS type thin-film semiconductor device to select column (MIS-$CS_{ij}$) as a column selection element ($CSE_{ij}$). In addition, a voltage Vdd is applied to the MIS type thin-film semiconductor device to amplify signal (MIS-$SA_{ij}$), the MIS type thin-film semiconductor device for row selection (MIS-$RS_{ij}$), and the MIS type thin-film semiconductor device for selecting column (MIS-$CS_{ij}$), which are coupled to the power-supply line ($PL_i$) in series. This enables a signal corresponding to electrostatic capacitance to be extracted in a short time, and further enables the interference of information caused between the electrostatic capacitance sensing elements (EC-$SE_{ij}$) to be reduced or prevented.

Figure 4:
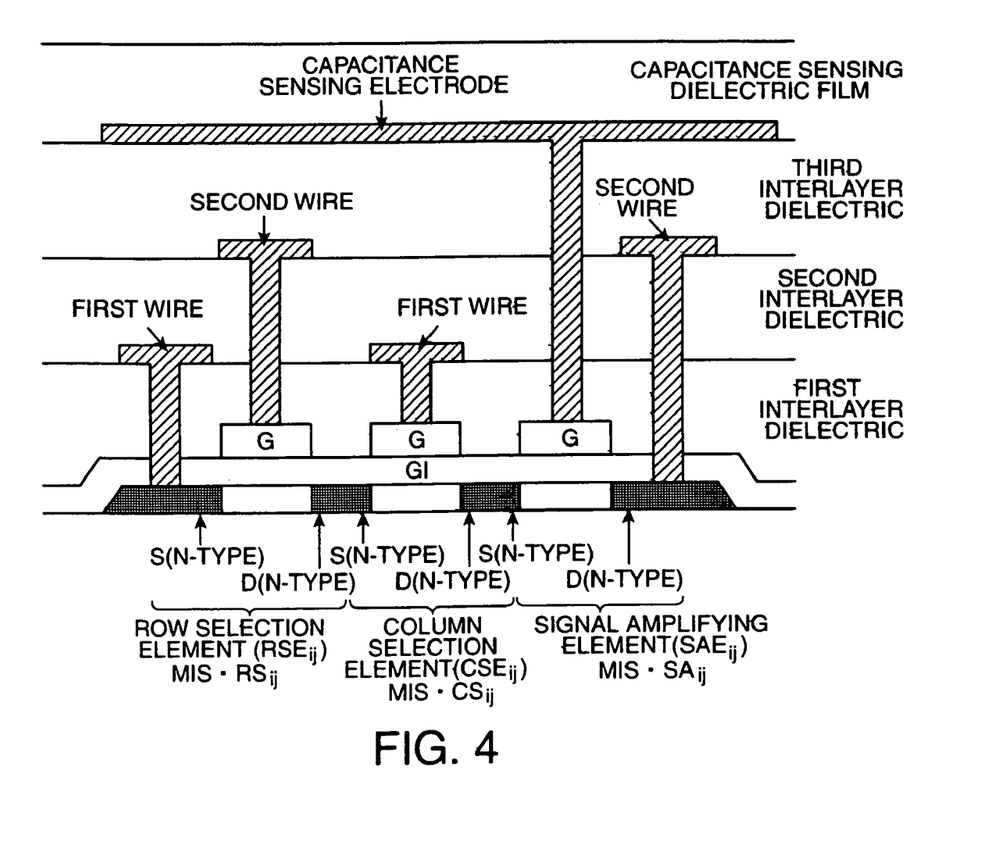
FIG. 4 is a schematic that shows the structure of an electrostatic capacitance sensing device of exemplary embodiments of the present invention.

A configuration of an electrostatic capacitance sensing element according to exemplary embodiments of this invention will be explained with reference to FIG. 4. Here, although all of thin-film semiconductor devices shown in FIG. 4 are illustrated as an N-type semiconductor, a P-type thin-film semiconductor device may be used. The MIS type thin-film semiconductor device to amplify signal (MIS-$SA_{ij}$) includes the signal amplifying element ($SAE_{ij}$), the MIS type thin-film semiconductor device for row selection (MIS-$RS_{ij}$) including the row selection element ($RSE_{ij}$), and the MIS type thin-film semiconductor device to select column (MIS-$CS_{ij}$) including the column selection element ($CSE_{ij}$), of the electrostatic capacitance sensing element (electrostatic capacitance sensing element $ECSE_{ij}$ located at the i-th row and the j-th column), important or essential structures are a gate insulation film, a gate electrode, and a semiconductor film that includes a source region, a channel formation region, and a drain region. A polycrystalline semiconductor film and a single-crystal semiconductor film are used for the semiconductor film. The main material of these films is silicon. In addition to pure silicon (Si), mixed semiconductor material including Si and impurities such as boron (B), phosphorus (P), and germanium (Ge) is also used. In the sample configuration depicted in FIG. 4, the MIS type thin-film semiconductor device to amplify signal (MIS-$SA_{ij}$), the MIS type thin-film semiconductor device for row selection (MIS-$RS_{ij}$), and the MIS type thin-film semiconductor device to select column (MIS-$CS_{ij}$) are covered by a first interlayer insulation film. A first wire is coupled to the source region of the MIS type thin-film semiconductor device for row selection (MIS-$RS_{ij}$) and the gate electrode of the MIS type thin-film semiconductor device for selecting column (MIS-$CS_{ij}$). A second wire is coupled to the drain region of the MIS type thin-film semiconductor device to amplify signal (MIS-SA$_{ij}$) and the gate electrode of the MIS type thin-film semiconductor device for row selection (MIS-RS$_{ij}$). A third wire is coupled to the gate electrode of the MIS type thin-film semiconductor device to amplify signal (MIS-SA$_{ij}$). (The first wire and second wire may be interchanged with each other. The drain region of the MIS type thin-film semiconductor device for row selection (MIS-RS$_{ij}$) and the source region of the MIS type thin-film semiconductor device to select column (MIS-CS$_{ij}$) are a common region. The same applies to the relationship between the drain region of the MIS type thin-film semiconductor device to select column (MIS-CS$_{ij}$) and the source region of the MIS type thin-film semiconductor device to amplify signal (MIS-SA$_{ij}$).)

A second interlayer dielectric is formed between the first wire and the second wire so as to electrically isolate the first wire and the second wire from one another. The capacitance sensing electrode, which constitutes the signal sensing element of the electrostatic capacitance sensing element, is coupled to the gate electrode of the MIS thin-film semiconductor device to amplify signal (MIS-SA$_{ij}$) with the third wire. A third interlayer insulation film is formed between the second wire and the capacitance sensing electrode so as to electrically isolate the second wire and the capacitance sensing electrode from one another. Exemplary embodiments of the present invention are directed to sense a minute signal, with respect to the element between the first or second wire and the electrostatic capacitance sensing element, such a structure that unnecessary parasitic capacitance is not caused, is adopted. Specifically, the ratio of the electrostatic capacitance $C_{ID}$ to the electrostatic capacitance $C_{CD}$ is set to be equal to or less than about 0.25. Here, $C_{ID}$ is the electrostatic capacitance per unit area of a dielectric (the third interlayer insulation film in FIG. 4) that isolates the capacitance sensing electrode from the wire (the second wire in FIG. 4) located as an closest under layer of the capacitance sensing electrode ($C_{ID}=\epsilon_0\epsilon_{ID}/d_{ID}$, where $\epsilon_0$ is the permittivity in vacuum, $\epsilon_{ID}$ is the dielectric constant of the isolation dielectric, $d_{ID}$ is the thickness of the isolation dielectric). $C_{CD}$ is the electrostatic capacitance per unit area of the capacitance sensing dielectric film ($C_{CD}=\epsilon_0\epsilon_{CD}/d_{CD}$, where $\epsilon_{CD}$ is the dielectric constant of the capacitance sensing dielectric film, $d_{CD}$ is the thickness of the capacitance sensing dielectric film). Namely, the ratio ($C_{ID}/C_{CD}=\epsilon_{ID}\cdot d_{CD}/\epsilon_{CD}\cdot d_{ID}$) is set to be about 0.25 or less. This enables wiring capacitance (the parasitic capacitance of the second wire and the capacitance sensing electrode in FIG. 4) to be decreased to the extent that it can be negligible even if the capacitance sensing electrode is miniaturized to about 30 μm square, enabling precise sensing of electrostatic capacitance. If this relationship is satisfied, electrostatic capacitance can be sensed with high sensitivity if the area of the capacitance sensing electrode is about 900 μm$^2$ or more. The capacitance sensing electrode is covered by the capacitance sensing dielectric film. The capacitance sensing dielectric film is located on the uppermost surface of the electrostatic capacitance sensing device. The capacitance sensing dielectric film simultaneously serves as a protective film for the electrostatic capacitance sensing device.

Although, in the structural example of the electrostatic capacitance sensing element of FIG. 4, the MIS type thin-film semiconductor device for row selection (MIS-RS$_{ij}$), the MIS type thin-film semiconductor device for selecting column (MIS-CS$_{ij}$), and the MIS type thin-film semiconductor device to amplify signal (MIS-SA$_{ij}$) are shown in this order from the left side of the drawing, this order can be changed. For example, from the left, the MIS type thin-film semiconductor device to select column (MIS-CS$_{ij}$), the MIS type thin-film semiconductor device to amplify signal (MIS-SA$_{ij}$), and the MIS type thin-film semiconductor device for row selection (MIS-RS$_{ij}$) may be arranged in this order. Thus, the number of arrangements in the electrostatic capacitance sensing element is the number of permutation of these three electrostatic capacitance sensing elements, namely, six. Among the thin-film semiconductor devices of three kinds, which are coupled to each other in series, a row selection element is the element whose gate electrode is coupled to a row line, a column selection element is the element whose gate electrode is coupled to a column line, and a signal amplifying element is the element whose gate electrode is coupled to a capacitance sensing electrode.

Figure 5:
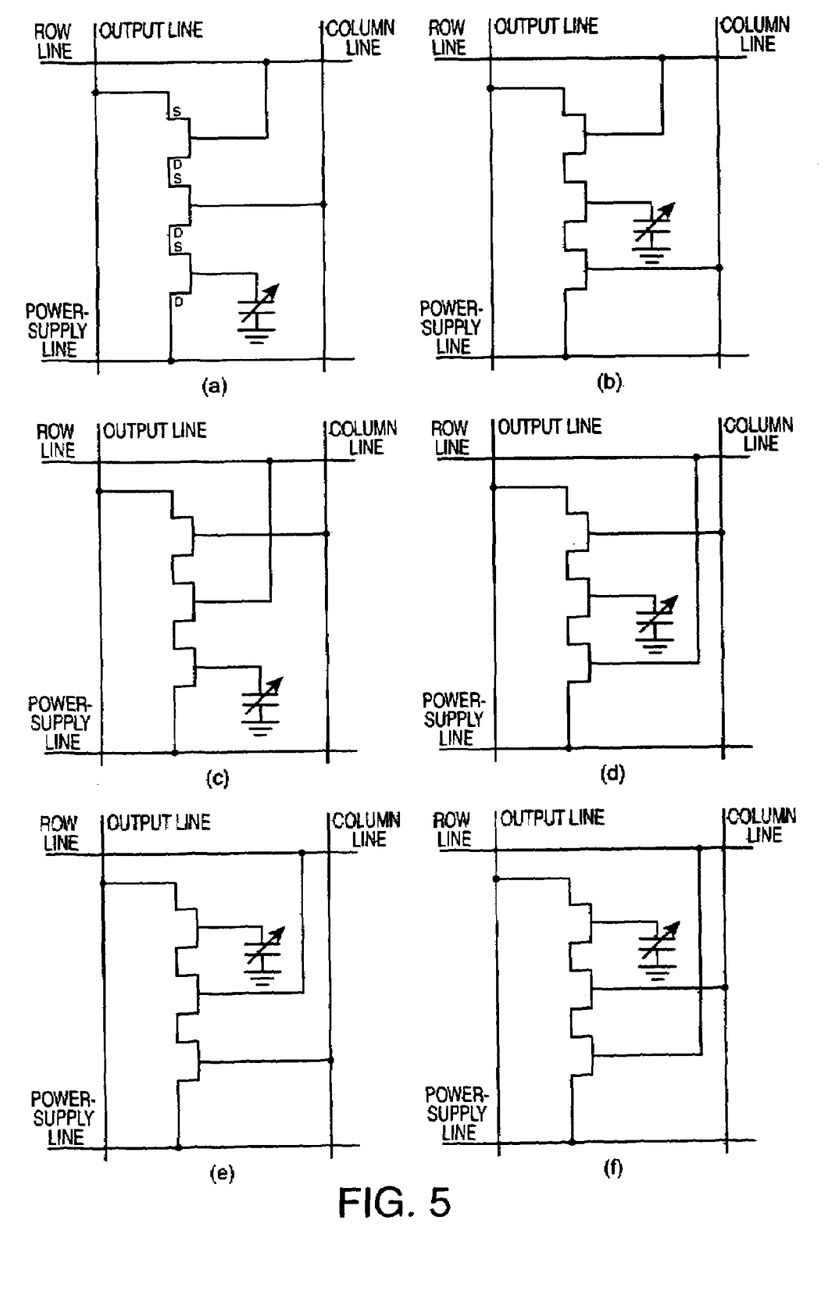
FIG. 5 is a schematic that shows the arrangements in the electrostatic capacitance sensing device that are possible in exemplary embodiments of the present invention.

FIG. 5 shows how these three elements are placed between an output line and a power-supply line. It is sufficient that three elements are coupled to each other in series between an output line and a power-supply line as depicted in FIGS. 5(*a*) through (*f*) regardless of the arrangement order. Although the conductive types of these three elements are not particularly limited, it is preferable that the conductive types of all three elements are the same, in order to miniaturize an element and increase the size of a capacitance sensing electrode so as to enhance sensing sensitivity.

Next, the overall configuration of an electrostatic capacitance sensing device according to exemplary embodiments of the present invention will be described with reference to FIG. 6. Here, shown is an example in which the number of power-supply lines (x) is the same as the number of row lines (M) (x=M), the number of output lines (y) is the number of column lines (N) (y=N), and the configuration shown in FIG. 5(*a*) is applied as the arrangement in electrostatic capacitance sensing elements. An electrostatic capacitance sensing device that reads the surface contours of a target object has, as minimum constituent elements, x number of power-supply lines (the power-supply line of the i-th row is represented as PL$_i$ where i is an integral number from 1 to x), and M number of row lines (the row line of the i-th row is represented as RL$_i$ where i is an integral number from 1 to M), y number of output lines (the output line of the j-th column is represented as OL$_j$ where j is an integral number from 1 to y), and N number of column lines (the column line of the j-th column is represented as CL$_j$ where j is an integral number from 1 to N) that are arranged in a matrix of M rows and N columns.

The sensing device also includes, as minimum constituent element, electrostatic capacitance sensing elements (the electrostatic capacitance sensing element located at the i-th row and the j-th column is represented as ECSE$_{ij}$) provided at the intersection between each row line (RL$_i$) and each column line (CL$_j$). In addition to these elements, the electrostatic capacitance sensing device may also include a row selection circuit that is coupled to the power-supply lines and the M number of row lines (RL$_i$), and a column selection circuit that is coupled to the output lines and the N number of column lines (CL$_j$). Although the number of power-supply lines, x, is the same as that of row lines, M, in the example of FIG. 6, the number of power-supply lines may be one per two rows (x=M/2 if M is an even number, x=(M+1)/2 if M is an odd number) or m−1 per m rows (2<m≦M) (M/2<x<M if M is an even number, (M+1)/2<x<M if M is an odd number) (for example, two lines per three rows, three lines per four rows, and so fourth). Similarly, although the number of output lines, y, is the same as that of column lines, N, in the example of FIG. 6, the number of output lines may be one per two columns (y=N/2 if N is an even number, y=(N+1)/2 if N is an odd number) or n−1 per n columns ($2<n\leq N$) ($N/2<y<N$ if N is an even number, $(N+1)/2<y<N$ if N is an odd number) (for example, two lines per three columns, three lines per four columns, and so fourth).

Figure 6:
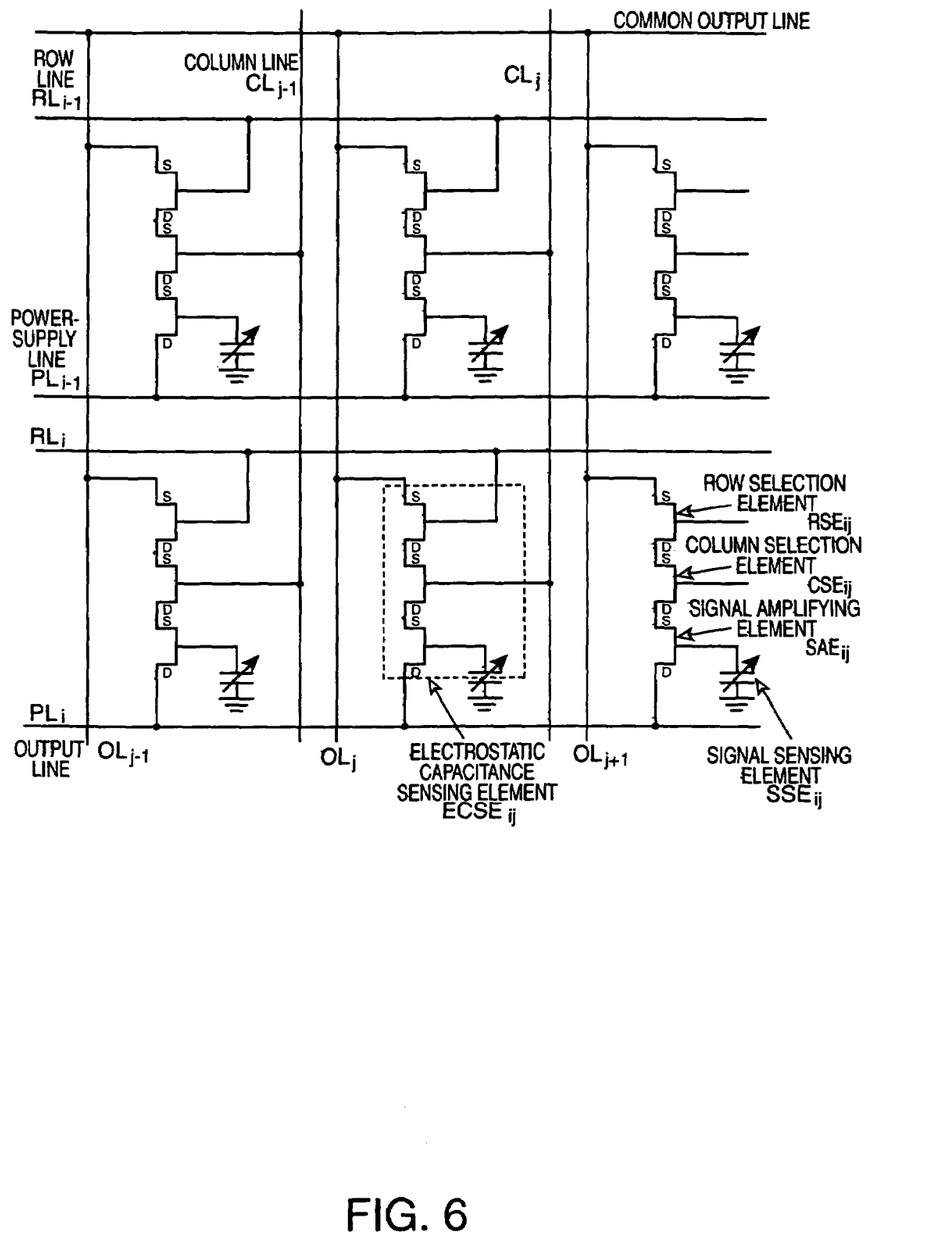
FIG. 6 is a schematic that shows the whole structure of the electrostatic capacitance sensing device according to exemplary embodiments of the present invention.
Figure 7:
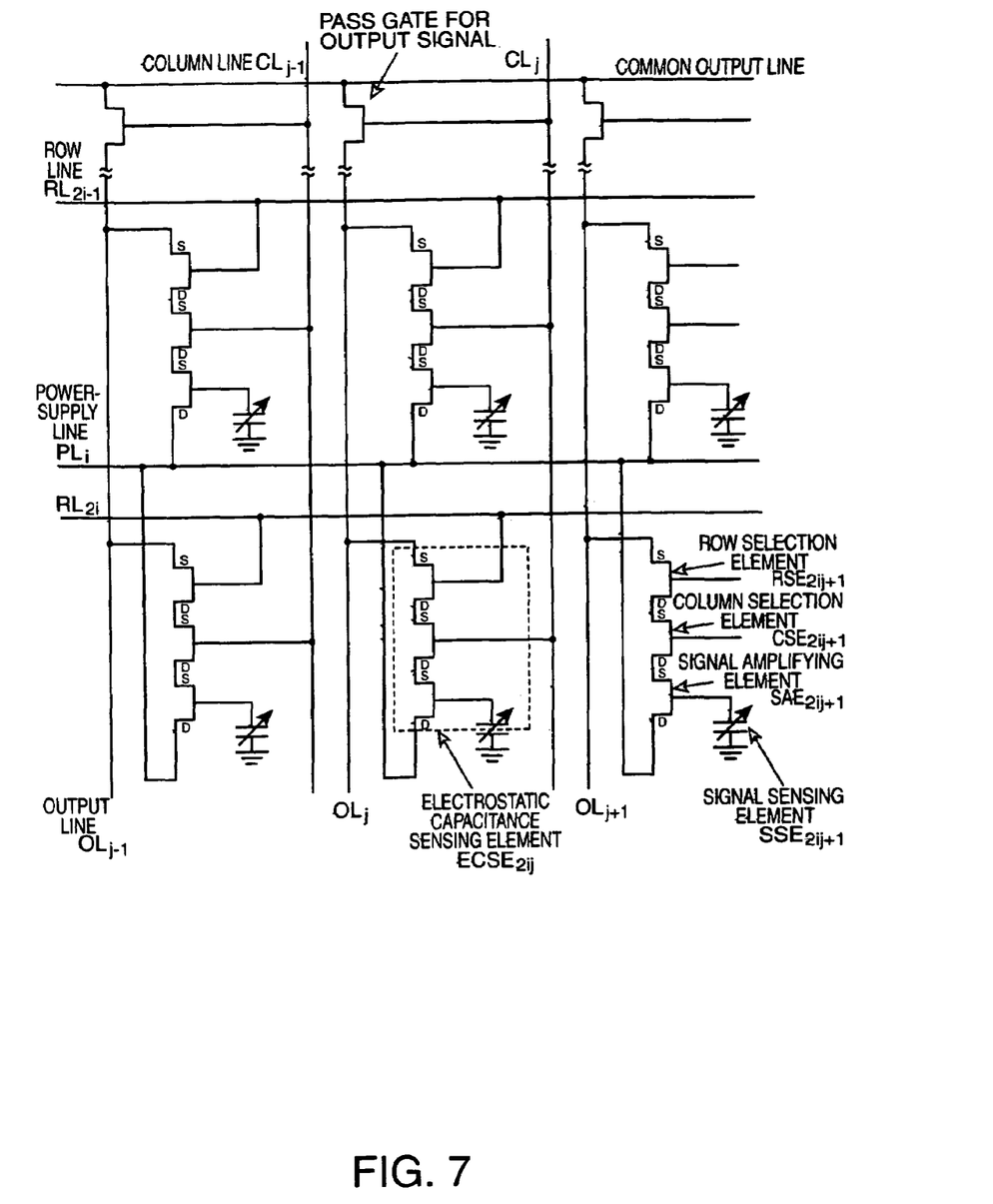
FIG. 7 is a schematic that shows the whole structure of the electrostatic capacitance sensing device according to exemplary embodiments of the present invention when the number of power-supply lines is one per two rows.

FIG. 7 shows a case in which the number of power-supply lines is one per two rows, based on the configuration of FIG. 6. In this case, for example, one power-supply line ($PL_i$) is disposed for adjacent two row lines of the row line ($RL_{2i-1}$) and the row line ($RL_{2i}$). When the electrostatic capacitance sensing element at the 2i–1-th row and the j-th column is selected by a row line and a column line, the power for the electrostatic capacitance sensing element at the 2i–1-th row and the j-th column is supplied from the power-supply line ($PL_i$) since the drain region of the signal amplifying element at the 2i–1-th row and the j-th column is coupled to the power-supply line ($PL_i$). Next, when the electrostatic capacitance sensing element at the 2i-th row and the j-th column is selected by a row line and a column line, the power for the electrostatic capacitance sensing element at the 2i-th row and the j-th column is also supplied from the power-supply line ($PL_i$) since the drain region of the signal amplifying element at the 2i-th row and the j-th column is also coupled to the same power-supply line ($PL_i$).

Figure 8:
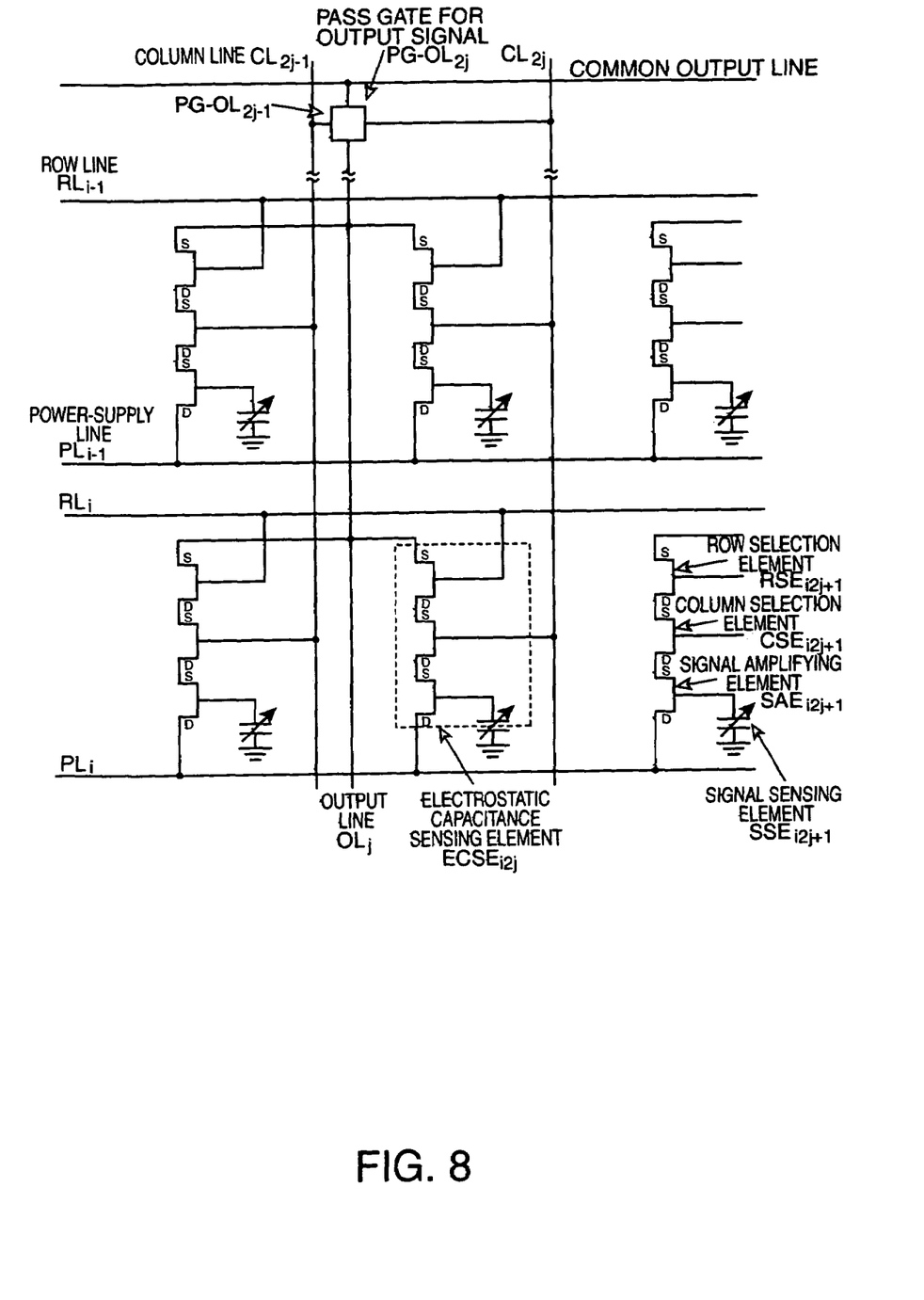
FIG. 8 is a schematic that shows the whole structure of the electrostatic capacitance sensing device according to exemplary embodiments of the present invention when the number of output lines is one per two columns.

FIG. 8 shows a case in which the number of output lines is one per two columns, based on the configuration of FIG. 6. In this case, for example, one output line ($OL_j$) is provided for adjacent two column lines of the column line ($CL_{2j-1}$) and the column line ($CL_{2j}$). Moreover, a pathgate for output signal ($PG-OL_{2j-1}$) and a pathgate for output signal ($PG-OL_{2j}$) are provided between a common output line and the output line ($OL_j$) in a manner of corresponding to the column line ($CL_{2j-1}$) and the column line ($CL_{2j}$), respectively. The number of the pathgates for output signal therefore becomes the same as that of the column lines. These two pathgates for output signal are coupled to each other in parallel, and when either of the column line ($CL_{2j-1}$) and the column line ($CL_{2j}$) is selected, corresponding one of the pathgates for output signal becomes conductive. Specifically, the pathgate for output signal ($PG-OL_j$) is made up of an MIS type thin-film semiconductor device for output signal pathgate ($MIS-PG_j$), and the gate electrode of the MIS type thin-film semiconductor device for output signal pathgate ($MIS-PG_j$) at the j-th column is coupled to the column line ($CL_j$) at the j-th column. Since the gate electrode of the MIS type thin-film semiconductor device to select column ($MIS-CS_{ij}$) in the electrostatic capacitance sensing element ($ECSE_{ij}$) located at the i-th row and the j-th column is also coupled to the column line ($CL_j$) at the j-th column, the column selection elements ($CSE_{ij}$) at the j-th column and the pathgate for output signal ($PG-OL_j$) at the j-th column perform the same switching operation.

In the example shown in FIG. 8, the gate electrode of the pathgate for output signal ($PG-OL_{2j-1}$) at the 2j–1-th column is coupled to the column line ($CL_{2j-1}$) at the 2j–1-th column, the source electrode is coupled to a common output line, and the drain electrode is coupled to the output line ($OL_j$) at the j-th column. Thus, when the column line ($CL_{2j-1}$) is selected, all of the MIS type thin-film semiconductor devices to select column ($MIS-CS_{i2j-1}$, i corresponds to all value from 1 to M) located at the 2j–1-th column perform the operation of switch-on, while the pathgate for output signal ($PG-OL_{2j-1}$) also performs the operation of switch-on simultaneously. When the electrostatic capacitance sensing element at the i-th row and the 2j–1-th column is selected by a row line and a column line, the output information from the electrostatic capacitance sensing element at the i-th row and the 2j–1-th column is output to the output line ($OL_j$), the path gate for output signal ($PG-OL_{2j-1}$), and the common output line sequentially in this order since the source region of the row selection element at the i-th row and the 2j–1-th column is coupled to the output line ($OL_j$). Next, when the electrostatic capacitance sensing element at the i-th row and the 2j-th column is selected by a row line and a column line, the output information from the electrostatic capacitance sensing element at the i-th row and the 2j-th column is output to the output line ($OL_j$), the path gate for output signal ($PG-OL_{2j}$), and the common output line sequentially in this order since the source region of the row selection element at the i-th row and the 2j-th column is also coupled to the same output line ($OL_j$). By adopting such a configuration, only one output line that has been selected is electrically coupled to the common output line always, and remaining y–1 number of output lines, which are not selected, are electrically isolated from the common output line. Since the common output line is coupled to an input node of a determining circuit such as a voltage comparator, the configuration of exemplary embodiments of the present invention allows physical quantity changes at the input node of the determining circuit to be accelerated such that the electrostatic capacitance of a target object can be sensed at high-speed. For example, in the case in which a voltage comparator is used as a determining circuit, the change regarding whether an input node becomes HIGH (around $V_{dd}$) or LOW (around $V_{ss}$) is speeded up such that the output from the determining circuit also becomes high-speed.

Figure 9:
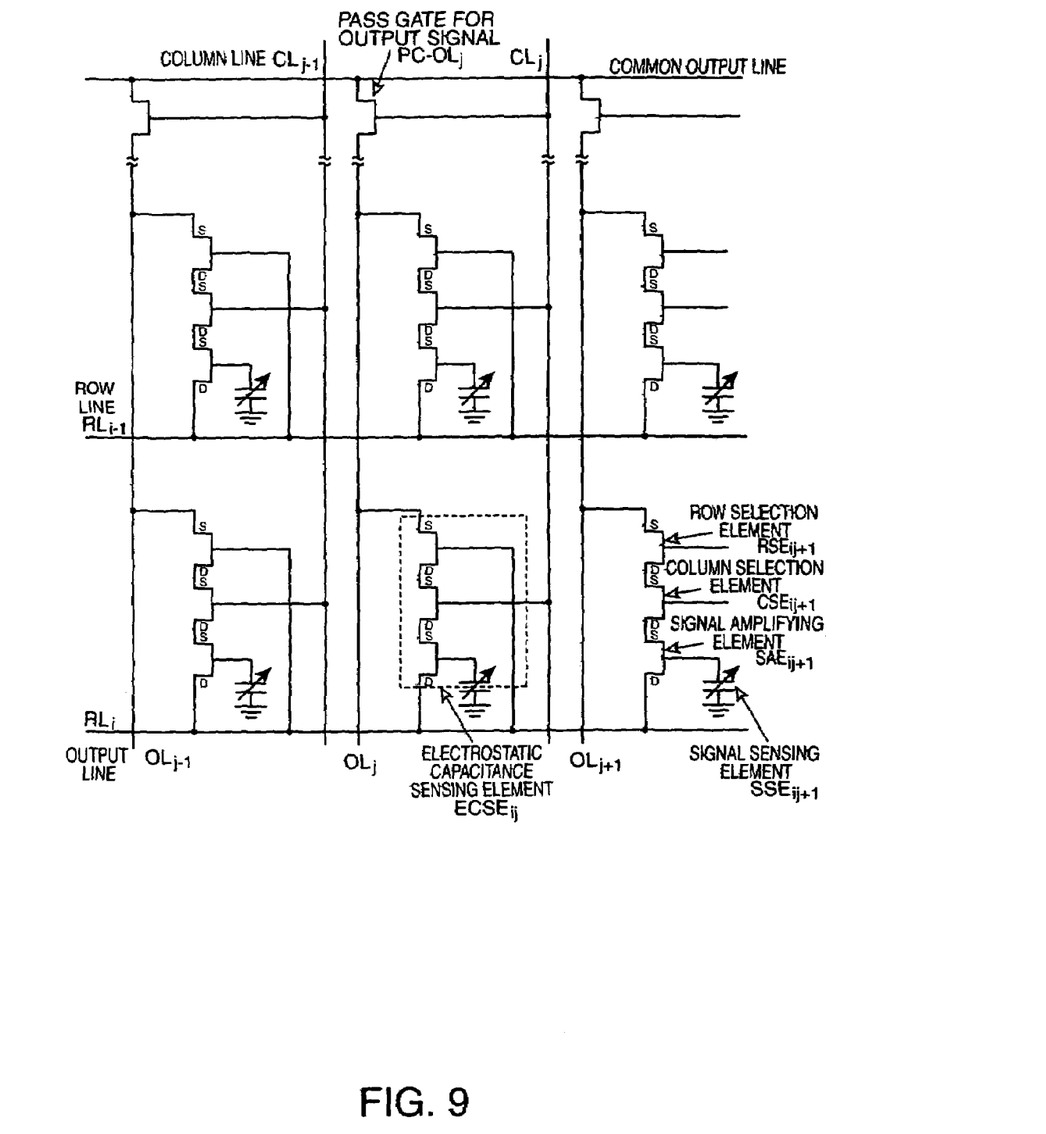
FIG. 9 is a schematic that shows the whole structure of the electrostatic capacitance sensing device according to exemplary embodiments of the present invention when the row lines also serve as power-supply lines.

In the configuration of exemplary embodiments of the present invention, the row line ($RL_i$) may have the combination of a function to select the MIS type thin-film semiconductor device for row selection ($MIS-RS_{ij}$) and a function of a power-supply line to supply power to an electrostatic capacitance sensing element. FIG. 9 shows a case in which the row line also serves as a power-supply line, based on the configuration of FIG. 6. In this case, the elements corresponding to the power-supply lines of FIG. 6 are omitted and the row lines also serve as power-supply lines. Accordingly, the gate electrode of the MIS type thin-film semiconductor device for row selection is coupled to the row line, while the drain region of the MIS type thin-film semiconductor device to amplify signal is also coupled to the row line. When the I–1-th row line is selected, among electrostatic capacitance sensing elements arranged in M rows and N columns, power is supplied to N number of electrostatic capacitance sensing elements ($ECSE_{i-1j}$) at the i–1-th row, and simultaneously all of the row selection elements ($RSE_{i-1j}$) located at the i–1-th row become a switch-on state. By sequentially scanning column lines in this state, the output information from the electrostatic capacitance sensing elements ($ECSE_{i-1j}$) at the i–1-th row is sequentially output to the common output line. Next, when the i-th row line is selected, among electrostatic capacitance sensing elements arranged in M rows and N columns, the supply of power to N number of the electrostatic capacitance sensing elements ($ECSE_{i-1j}$) at the i–1-th row is stopped, and simultaneouly the row selection elements ($RSE_{i-1j}$) located at the i-th row become a switch-off state. In addition, power is supplied to N number of the electrostatic capacitance sensing elements ($ECSE_{ij}$) at the i-th row, and simultaneously the row selection elements ($RSE_{ij}$) become a switch-on state. By sequentially scanning column lines in this state as with the i–1-th row, the output information from the electrostatic capacitance sensing elements ($ECSE_{ij}$) at the i-th row is sequentially output to the common output line. Even in the case in which row lines also serve as power-supply lines, as shown in FIG. 8, the number of output lines can be one per two columns, or n-1 per n (2<n≦N) columns (N/2<y<N if N is an even number, (N+1)/2<y<N if N is an odd number) (for example, two per three columns, three per four columns). It is also possible to add any number (0≦x≦M) of power-supply lines. Namely, the following configuration is also possible for example: the gate electrodes of the MIS type semiconductor devices for row selection and the drain regions of the MIS type semiconductor devices to amplify signal, at the i-2-th row, i-1-th row, and the i+1-th row, are coupled to row lines that also serve as power-supply lines, while the gate electrode of the MIS type semiconductor device for row selection at the i-th row is coupled to a row line, and the drain region of the MIS type semiconductor device to amplify signal at the i-th row is coupled to a power-supply line.

An electrostatic capacitance sensing element includes a signal sensing element ($SSE_{ij}$) that is made up of a capacitance sensing electrode and a capacitance sensing dielectric film, a signal amplifying element ($SAE_{ij}$), a row selection element ($RSE_{ij}$), and a column selection element ($CSE_{ij}$). In order to read the surface contours of a target object, M×N numbers of electrostatic capacitance sensing elements need to be selected in an appropriate order by sequentially scanning rows and columns. A row selection circuit determines the order of supplying a row selection signal to each electrostatic capacitance sensing element. The row selection circuit includes at least a common power-supply line so as to be coupled to power-supply lines extended in a matrix. Both of a positive and negative power supplies can be used as a power supply. In the case in which semiconductor devices constituting an electrostatic capacitance sensing element are an N-type, the potential of the positive power supply is plus (for example, +2.5 V or +3.3 V) and the potential of the negative power supply is ground potential (0 V). On the contrary, in the case in which semiconductor devices constituting an electrostatic capacitance sensing element are a P-type, the potential of the positive power supply is ground potential (0 V) and the potential of the negative power supply is minus (for example, -2.5 V or -3.3 V). The potential of the power-supply line is always adverse to the potential coupled to an end of the common output line. For example, if electrostatic capacitance sensing elements are N-type semiconductor devices and a positive potential is coupled to power-supply lines, a negative power supply is coupled to an end of the common output line such that the direction of a current in the electrostatic capacitance sensing element is from the power-supply line to the common output line. Contrary to this, if a negative potential is coupled to power-supply lines, a positive power supply is coupled to the common output line such that the direction of a current in the electrostatic capacitance sensing element is from the common output line to the power-supply line.

The row selection circuit selects which of M number of row lines ($RL_i$) to which a selection signal is supplied. Namely, the row selection circuit applies a positive supply potential to certain one row line selected from M number of row lines and keeps other row lines, which are in a non-selected state, be at a negative supply potential. As a result, row selection elements coupled to the selected row line become a switch-on state such that these row selection elements enhance the electrical conductivity thereof.

A column selection circuit determines the order of supplying a column selection signal to each electrostatic capacitance sensing element. The column selection circuit applies a positive supply potential to certain one column line selected from N number of column lines and keeps other column lines, which are in a non-selected state, at a negative supply potential. This makes column selection elements coupled to the selected column line become a switch-on state such that these column selection elements enhance the electrical conductivity thereof. Since the row selection element, the column selection element, and the signal amplifying element are coupled to each other in series, only an electrostatic capacitance sensing element for which the row and column are selected simultaneously changes the electrical conductivity of the power-supply line and the output line according to the signal amplifying element.

The column selection circuit includes at least a path gate for output signal and a common output line. The column selection circuit selects which of columns from which an output signal is extracted, simultaneously with supplying a selection signal to any of N number of column lines ($CL_j$). Output lines extended in the electrostatic capacitance sensing device are coupled to the common output line with the path gates for output signal. The gate electrode of the path gate for output signal ($PG\text{-}OL_j$) located at the j-th column is coupled to the column line ($CL_j$) at the j-th column, the source electrode is coupled to the common output line, and the drain electrode is coupled to the output line ($OL_j$) to which the electrostatic capacitance sensing element at the j-th column is coupled. Since the output line is one-to-one provided for each column line (y=N) in the sample configuration of FIG. 6, the source electrode of the path gate for output signal ($PG\text{-}OL_j$) is coupled to the output line ($OL_j$) at the j-th column. In the case in which the number of output lines is one per two columns, the group of electrostatic capacitance sensing elements at the 2j-1-th column and the group of electrostatic capacitance sensing elements at the 2j-th column share the output line ($OL_j$) at the j-th column, and the path gate for output signal ($PG\text{-}OL_{2j-1}$) at the 2j-1-th column and the path gate for output signal ($PG\text{-}OL_{2j}$) at the 2j-th column are coupled to the output line ($OL_j$) at the j-th column in parallel. Of course the gate electrode of the path gate for output signal ($PG\text{-}OL_{2j-1}$) at the 2j-1-th column is coupled to the column line ($CL_{2j-1}$) at the 2j-1-th column, while the gate electrode of the path gate for output signal ($PG\text{-}OL_{2j}$) at the 2j-th column is coupled to the column line ($CL_{2j}$) at the 2j-th column. The path gate for output signal and the column selection element perform the same switching operation by a column selection signal supplied to a column line. Namely, when the column selection elements ($CSE_j$) located at the j-th column are in a switch-on state, the path gate for output signal ($PG\text{-}OL_j$) at the j-th column is also in a switch-on state.

In exemplary embodiments of the present invention, since each electrostatic capacitance sensing element includes a row selection element and a column selection element, and only a certain electrostatic capacitance sensing element is selected by timely selecting of a row line and a column line, electrostatic capacitance that changes according to ridges and valleys of a target object can be sensed by directly coupling all output lines to a common output line collectively and providing measurement equipment at an end of the common output line. However, in such a configuration, since all output lines are coupled to each other, a current output from a selected electrostatic capacitance sensing element needs to charge all parasitic electrostatic capacitance incidental to all output lines, slowing sensing speed.

Thus, in exemplary embodiments of the present invention, a path gate for output signal is also selected simultaneously with selecting of a column. According to this, when a certain column line is selected, only the output line coupled to the selected column line is electrically coupled to the common output line. The parasitic capacitance incidental to output lines therefore diminishes remarkably such that it becomes possible to obtain parasitic capacitance information in a short time. If the number of output lines is y, the above configuration of exemplary embodiments of the present invention enable the parasitic capacitance incidental to the output lines to be decreased to about one y-th. In an electrostatic capacitance sensing device of a matrix, the number of column lines is generally about several hundreds (from 200 to 1000) such that the number of output lines is also about several hundreds (y is from 100 to 1000). Thus, according to the configuration of exemplary embodiments of the present invention, the parasitic capacitance incidental to the output lines, which needs to be charged, is decreased to value ranging between one hundredth and one thousandth thereof. In other words, fixing of measurement time allows sensing sensitivity to be enhanced by 100–1000 times, while fixing of sensing sensitivity allows measurement time to be shortened to an amount ranging between one hundredth and one thousandth thereof. Thus, the configuration of exemplary embodiments of the present invention enables the sensing of electrostatic capacitance at high speed and with high sensitivity.

In each electrostatic capacitance sensing element, the gate electrode of the MIS type thin-film semiconductor device for row selection (MIS-RS$_{ij}$) is coupled to the row line (RL$_i$). The gate electrode of the MIS type thin-film semiconductor device for selecting column (MIS-CS$_{ij}$) is coupled to the column line (CL$_j$). The gate electrode of the MIS type thin-film semiconductor device to amplify signal (MIS-SA$_{ij}$) is coupled to the capacitance sensing electrode. In such a condition, three thin-film semiconductor devices are coupled to each other between a power-supply line and an output line. In the example shown in FIG. 6, the source region of the MIS type thin-film semiconductor device for row selection (MIS-RS$_{ij}$) is coupled to the output line (OL$_j$), and the drain region of the MIS type thin-film semiconductor device for row selection (MIS-RS$_{ij}$) is coupled to the source region of the MIS type thin-film semiconductor device to select column (MIS-CS$_{ij}$). In addition, the drain region of the MIS type thin-film semiconductor device to select column (MIS-CS$_{ij}$) is coupled to the source region of the MIS type thin-film semiconductor device to amplify signal (MIS-SA$_{ij}$), and the drain region of the MIS type thin-film semiconductor device to amplify signal (MIS-SA$_{ij}$) is coupled to the power-supply line (PL$_i$). Thus, the power-supply line (PL$_i$) and the output line (OL$_j$) are coupled to one another with the interposition of a channel-forming region that responds to the charge Q sensed at the capacitance sensing electrode.

The row line (RL$_i$) and the column line (CL$_j$) can be each output stage of a shift register as one example, or can be each output stage of a decoder instead of a shift register. A shift register sequentially supplies a selection signal that has been transferred to M or N number of output stages. Also, a decoder selects a specific output stage from the M or N number of output stages according to the signal input to the decoder. Thus, a selection signal is timely input to the i-th row line (RL$_i$) so as to select N number of MIS type thin-film semiconductor devices for row selection (MIS-RS$_{ij}$). Subsequently, a selection signal is sequentially input to the j-th column line (CL$_j$) such that the j-th path gate for output signal and the only one MIS type thin-film semiconductor device to select column (MIS-CS$_{ij}$) are selected. Thus, a current corresponding to the surface contours of a target object is supplied to the common output line through the output line (OL$_j$) and the path gate for output signal. Thereafter, by similarly sequentially scanning the N number of column lines (CL$_j$) in a state where only one of the M number of row lines (RL$_i$) is selected, signals from the electrostatic capacitance sensing elements arranged in an array of M rows and N columns are sequentially supplied to the common output line. Specifically, in the case in which semiconductor devices constituting an electrostatic capacitance sensing element are an N-type, when a voltage that is high with respect to ground voltage is applied to the selected row line (RL$_i$), the MIS type thin-film semiconductor devices for row selection (MIS-RS$_{ij}$) become conductive so as to be in a switch on state. In addition, when a voltage that is high with respect to ground voltage is applied to the selected column line (CL$_j$), the MIS type thin-film semiconductor device to select column (MIS-CS$_{ij}$) becomes conductive so as to be in a switch-on state. Only the signal amplifying element (SAE$_{ij}$) coupled to the row line (RL$_i$) and the column line (CL$_j$) that have been selected in this manner supplies a current (signal current) correspnding to the surface contours of a target object to the output line.

A path gate for output signal is provided for the output line, and the path gate for output signal (PG-OL$_j$) coupled to the selected column line (CL$_j$) becomes conductive so as to be in a switch-on state Thus, a signal current reaches the common output line through the path gate for output signal (PG-OL$_j$). In the case in which semiconductor devices constituting an electrostatic capacitance sensing element are a P-type, when a voltage that is minus with respect to ground voltage is applied to the selected row line (RL$_i$), the MIS type thin-film semiconductor devices for row selection (MIS-RS$_{ij}$) become conductive. In addition, when a voltage that is minus with respect to ground voltage is applied to the selected column line (CL$_j$), the MIS type thin-film semiconductor device to select column (MIS-CS$_{ij}$) becomes conductive. Only the signal amplifying element (SAE$_{ij}$) coupled to the row line (RL$_i$) and the column line (CL$_j$) that have been selected in this manner supplies a current (signal current) coresponding to the surface contours of a target object to the output line. A path gate for output signal is provided for the output line, and the path gate for output signal (PG-OL$_j$) coupled to the selected column line (CL$_j$) becomes conductive so as to be in a switch-on state. Thus, a signal current reaches the common output line through the path gate for output signal (PG-OL$_j$). Here, although columns are scanned after a row is selected in the above, rows may be scanned after a column is selected.

The forgoing explanation has been made on the premise that thin-film semiconductor devices are an N-type mainly (for example, FIG. 6). However, P-type thin-film semiconductor devices may be used of course. Moreover, the foregoing explanation has been made on the premise that power-supply lines and output lines are arranged along rows and columns, respectively. However, power-supply lines and output lines may be arranged along columns and rows, respectively.

As above, since the electrostatic capacitance sensing device of exemplary embodiments of the present invention is made up of thin-film transistors, the electrostatic capacitance sensing device can be fabricated on a plastic substrate by using the above SUFTLA technique. A fingerprint sensor based on single-crystal silicon technology would have very little practical application, since it would promptly break on plastic, or it would not possess sufficient size. In contrast to this, an electrostatic capacitance sensing element formed on a plastic substrate according to exemplary embodiments of the present invention will not break even if the area is sufficiently large to cover a fingertip on the plastic substrate. Hence, exemplary embodiments of the present invention can be used as a fingerprint sensor on a plastic substrate. Specifically, exemplary embodiments of the present invention enable the realization of a smart card equipped with a personal identification function. Used in cash cards (bank cards), credit cards, identify cards, and so forth, smart cards equipped with a personal identification function have the superior feature of not only markedly enhancing or improving the security level of these cards but also of protecting personal fingerprint information from being released outside the card.

An electrostatic capacitance sensing device made up of thin-film semiconductor devices was fabricated on a glass substrate. The fabricated electrostatic capacitance sensing device was then transferred to a plastic substrate using the SUFTLA technology. The electrostatic capacitance sensing device includes electrostatic capacitance sensing elements aligned in a matrix of 304 rows and 304 columns. The array is a square having a diagonal measurement of 20.32 mm.

The substrate, made of poly-ether-sulfone (PES), has a thickness of 400 µm. The row selection element, the column selection element, the signal amplifying element, and the MIS type thin-film semiconductor device that constitutes a shift register are all fabricated with thin-film transistors having the same sectional structure. The thin-film transistors are a top-gate type, as shown in FIG. 4. They are fabricated in a low-temperature process where the maximum process temperature is 425 degrees centigrade. The semiconductor film is a polycrystalline silicon thin-film achieved through laser crystallization, and has a thickness of 59 nm. In addition, the gate insulation film is a silicon-oxide layer having a thickness of 45 nm that was formed by chemical vapor deposition (CVD). The gate electrode is made up of a 400-nm-thick tantalum thin-film. The dielectric constant of the silicon-oxide film that forms the gate insulation film was found to be approximately 3.9 according to CV measurement. A first interlayer insulation film and second interlayer insulation film are silicon-oxide films that were deposited by CVD using tetra-ethyl-ortho-silicate (TEOS: Si (OCH$_2$CH$_3$)$_4$) and oxygen as source gases. It is preferable that the first interlayer insulation film is approximately at least 20% thicker than the gate electrode (400 nm in this exemplary embodiment) and is thinner than the second interlayer insulation film. This is because, when made this way, the first interlayer insulation film surely covers the gate electrode, reduces or prevents short-circuits between the gate electrode and the first wire or the second wire, and at the same time enables the second interlayer insulation film to be deposited to a greater thickness. In this exemplary embodiment, the thickness of the first interlayer insulation film was 500 nm. A third interlayer insulation film isolates the second wire from a capacitance sensing electrode so as to reduce or prevent short-circuit. The first wire and the capacitance sensing electrode are isolated from each other by the second and third interlayer insulation films. Therefore, to minimize the parasitic capacitance that exists between the first wire and the capacitance sensing electrode and to realize a highly sensitive electrostatic capacitance sensing device, the dielectric constants of the second and third interlayer insulation films are preferably as small as possible and the thicknesses thereof are preferably as thick as possible. However, if the total thickness of the silicon-oxide film deposited by CVD exceeds about 2 µm, fissures may develop in the oxide layer, bringing reduced yield. Therefore, the first, second, and third interlayer insulation films are deposited in such a manner that the sum of their respective thicknesses is approximately 2 µm or less. Thus, the productivity of the electrostatic capacitance sensing device can be enhanced or improved.

As stated above, the second and third interlayer insulation films are preferably thick and, thus, are made thicker than the first interlayer insulation film. Ideally, the first interlayer insulation film is approximately at least 20% thicker than the gate electrode, the second and third interlayer insulation films are thicker than the first interlayer insulation film, and the sum of the thicknesses of the first, second, and thrid interlayer insulation films is approximately 2 µm or less. In this exemplary embodiment, the thickness of the second interlayer insulation film is 1 µm. The first wire and the second wire are both made of 500-nm-thick aluminum. The wires are 5 µm in width. The common output line, the output line, and the column line are made up of the first wire. The common power-supply line, the power-supply line, and the row line are made up of the second wire. The capacitance sensing electrode is made up of the third wire. The gap between a power-supply line and a capacitance sensing electrode is 5 µm. Likewise, the gap between an output line and a capacitance sensing electrode is also 5 µm. In this exemplary embodiment, the pitch of the rows and columns that form the electrostatic capacitance sensing device is 66.7 µm, and the resolution is 381 dpi (dots per inch). Therefore, the capacitance sensing electrode is 55.0 µm×55.0 µm in size. The capacitance sensing dielectric film is formed by a silicon-nitride film having a thickness of 400 nm. Since CV measurement showed the dielectric constant of the silicon-nitride film to be approximately 7.5, the element capacitance $C_D$ is approximately 574 fF (femtofarad). Assuming that the electrostatic capacitance sensing device of this exemplary embodiment is a fingerprint sensor, since the difference in height between the ridges and valleys in a fingerprint is approximately 50 µm, the target object capacitance $C_A$ when a valley in a fingerprint is present over the surface of the electrostatic capacitance sensing device is calculated to be 0.54 fF. Meanwhile, because the gate electrode length L of the MIS type thin-film semiconductor device for amplifying signal was set to 7 µm, and the gate electrode width W was set to 10 µm, the transistor capacitance $C_T$ is approximately 53.7 fF. If the power supply voltage $V_{dd}$ is 3.3V, then 0.16V is the voltage $V_{GT}$ applied to the gate electrode of the MIS type thin-film semiconductor device to amplify signal when ridges in a fingerprint touch the surface of the electrostatic capacitance sensing device; and 3.22V is the voltage $V_{GV}$ applied to this gate electrode when a valley in a fingerprint is present.

The row selection element, the column selection element, and the signal amplifying element were coupled to each other in series, and were disposed between the power-supply line and the output line. The positional relationship of these elements was the same as that shown in FIG. 5(*a*). All of the row selection element, the column selection element, and the signal amplifying element were made up of an NMOS thin-film transistor. A negative power (ground potential) was applied to the power-supply line. The output line was coupled to the common output line via a path gate for output. Measurement equipment made up of an ammeter was provided for an end of the common output line. A further end of the common output line was coupled to a positive power-supply (Vdd =+3.3 V). Accordingly, when the electrostatic capacitance sensing device of exemplary embodiments of the present invention is used as a fingerprint sensor, and a valley in a fingerprint is present over the sensor surface, a current transmits in the common output line, the path gate for output, the output line, the row selection element, the column selection element, and the signal amplifying element in this order, from a positive power-supply through an ammeter, so as to reach the power-supply line coupled to a negative power-supply.

Figure 10:
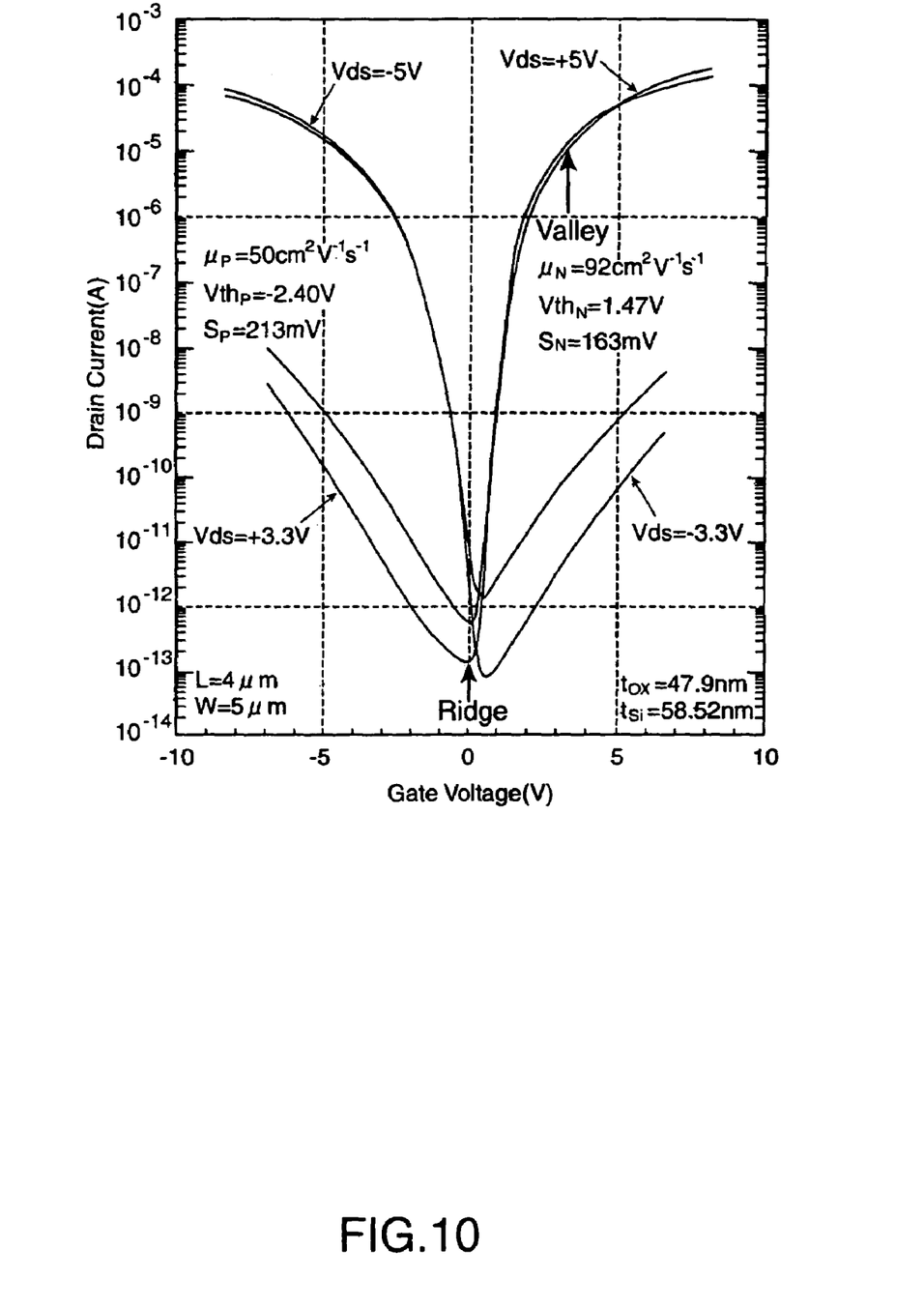
FIG. 10 is a schematic that shows the transfer characteristics diagram of the thin-film semiconductor device used in a working example.

FIG. 10 illustrates the transfer characteristics of an MIS type thin-film semiconductor device used in this exemplary embodiment. The structure of the shift register for output signal was a CMOS structure. The MIS type thin-film semiconductor device to amplify signal, the MIS type thin-film semiconductor device for row selection, and the MIS type thin-film semiconductor device to select column are made up of an NMOS transistor. As a result, the current value that is output from a signal amplifying element when a ridge in a fingerprint touches the surface of the electrostatic capacitance sensing device is, at 5.6×10$^{-13}$ A, exceedingly small. Conversely, when a valley in a fingerprint is present, a large current of 2.4×10$^{-5}$ A is output from the signal amplifying element. Hence ridge and valley information for objects such as fingerprints was detected with high accuracy and precision.

Exemplary embodiments of the present invention are utilized for an electrostatic capacitance sensing device that reads the surface contours of a fingerprint or other target object having extremely small ridges and valleys, by sensing electrostatic capacitance, which changes according to the distance from the surface of the target object. Specifically, exemplary embodiments of the present invention are utilized as an electrostatic capacitance image-capturing device such as a fingerprint sensor.

What is claimed is:

1. An electrostatic capacitance sensing device, the device comprising:

M number of row lines;

N number of column lines; and electrostatic capacitance sensing elements formed at intersections between the row lines and the column lines, and arranged in a matrix of M rows and N columns, each of the electrostatic capacitance sensing elements including a signal sensing element, a signal amplifying element, a row selection element, and a column selection element;

the signal sensing element including a capacitance sensing electrode and a capacitance sensing dielectric film;

the signal amplifying element being a semiconductor device to amplify a signal that includes a gate electrode, a gate insulation film, and a semiconductor film;

the row selection element being a semiconductor device for row selection that includes a gate electrode, a gate insulation film, and a semiconductor film;

the column selection element being a semiconductor device to select a column that includes a gate electrode, a gate insulation film, and a semiconductor film, and the semiconductor device to amplify a signal, the semiconductor device for row selection, and the semiconductor device to select the column being coupled to each other in series, wherein:

the gate electrode of the MIS type thin-film semiconductor device to amplify a signal being coupled to the capacitance sensing electrode;

the gate electrode of the MIS type thin-film semiconductor device for row selection being coupled to one of the row lines; and the gate electrode of the MIS type thin-film semiconductor device to select a column being coupled to one of the column lines.

2. The electrostatic capacitance sensing device according to claim 1, the following relationship being satisfied:

x=M, where x is a number of power-supply lines.

3. The electrostatic capacitance sensing device according to claim 1, the following relationship being satisfied:

x=M/2, where x is a number of power-supply lines.

4. The electrostatic capacitance sensing device according to claim 1, the following relationship being satisfied:

M/2<x<M, where x is a number of power-supply lines.

5. The electrostatic capacitance sensing device according to claim 1, the following relationship being satisfied:

y=N, where y is a number of output lines.

6. The electrostatic capacitance sensing device according to claim 1, the following relationship being satisfied:

y=N/2, where y is a number of output lines.

7. The electrostatic capacitance sensing device according to claim 1, the following relationship being satisfied:

N/2<y<N, where y is a number of output lines.

8. The electrostatic capacitance sensing device according to claim 1, the semiconductor device to amplify a signal being disposed between the semiconductor device for row selection and the semiconductor device to select the column.

9. An electrostatic capacitance sensing device, the device comprising:

M number of row lines;

N number of column lines;

a path gate for an output signal; and electrostatic capacitance sensing elements formed at intersections between the row lines and the column lines, and arranged in a matrix of M rows and N columns, each of the electrostatic capacitance sensing elements including a signal sensing element, a signal amplifying element, a row selection element, and a column selection element;

the path gate for output signal being a semiconductor device for output signal pass gate that includes a gate electrode, a gate insulation film, and a semiconductor film;

the signal sensing element including a capacitance sensing electrode and a capacitance sensing dielectric film;

the signal amplifying element being a semiconductor device to amplify a signal that includes a gate electrode, a gate insulation film, and a semiconductor film;

the row selection element being a semiconductor device for row selection that includes a gate electrode, a gate insulation film, and a semiconductor film;

the column selection element being a semiconductor device to select a column that includes a gate electrode, a gate insulation film, and a semiconductor film, the semiconductor device to amplify a signal, the semiconductor device for row selection, and the semiconductor device to select a column being coupled to each other in series, the gate electrode of the MIS type thin-film semiconductor device to amplify a signal being coupled to the capacitance sensing electrode, the gate electrode of the MIS type thin-film semiconductor device for row selection being coupled to one of the row lines, and the gate electrode of the MIS type thin-film semiconductor device to select a column being coupled to one of the column lines.

10. The electrostatic capacitance sensing device according to claim 9, the following relationship being satisfied:

x=M, where x is a number of power-supply lines.

11. The electrostatic capacitance sensing device according to claim 9, the following relationship being satisfied:

x=M/2, where x is a number of power-supply lines.

12. The electrostatic capacitance sensing device according to claim 9, the following relationship being satisfied:

M/2<x<M, where x is a number of power-supply lines.

13. The electrostatic capacitance sensing device according to claim 9, the following relationship being satisfied:

y=N, where y is a number of output lines.

14. The electrostatic capacitance sensing device according to claim 9, the following relationship being satisfied:

y=N/2, where y is a number of output lines.

15. The electrostatic capacitance sensing device according to claim 9, the following relationship being satisfied:

N/2<y<N, where y is a number of output lines.

16. The electrostatic capacitance sensing device according to claim 9, the semiconductor device to amplify a signal being disposed between the semiconductor device for row selection and the semiconductor device to select the column.

* * * * *